(12) United States Patent  
Reed

(10) Patent No.: US 8,091,848 B1
(45) Date of Patent: Jan. 10, 2012

(54) HANDS FREE SPECIMEN HOLDER APPARATUS AND METHOD

(76) Inventor: Rachel Gail Reed, Pensacola Beach, FL (US)

( * ) Notice: Subject to any disclaimer, the term of this patent is extended or adjusted under 35 U.S.C. 154(b) by 291 days.

(21) Appl. No.: 12/288,093

(22) Filed: Oct. 16, 2008

(51) Int. Cl.
*A47K 1/08* (2006.01)
(52) U.S. Cl. ........................ 248/311.2; 248/312; 220/737
(58) Field of Classification Search ............... 248/311.2, 248/312, 103, 102, 312.1; 220/737, 752; 215/396, 395; 16/425, 422, 430; D9/455
See application file for complete search history.

(56) References Cited

U.S. PATENT DOCUMENTS

| 4,779,831 | A | * | 10/1988 | Anderson | 248/311.2 |
| 4,865,237 | A | * | 9/1989 | Allen | 224/552 |
| 5,058,787 | A | * | 10/1991 | Chou | 224/556 |
| 5,865,412 | A | * | 2/1999 | Mason | 248/311.2 |
| 5,938,160 | A | * | 8/1999 | Hartmann et al. | 248/311.2 |
| 2004/0200943 | A1 | * | 10/2004 | Rokov | 248/311.2 |
| 2005/0199770 | A1 | * | 9/2005 | Andrews | 248/311.2 |
| 2007/0151460 | A1 | * | 7/2007 | Beck | 99/279 |

* cited by examiner

*Primary Examiner* — A. Joseph Wujciak, III
(74) *Attorney, Agent, or Firm* — J. Nevin Shaffer, Jr.

(57) ABSTRACT

A hands free specimen holder apparatus includes a cup holder. An arm is connected with the cup holder at a first end and the arm extends the cup holder from the first end and away from and below a second end. The second end of the arm is conformed to connect with a toilet seat.

13 Claims, 2 Drawing Sheets

HANDS FREE SPECIMEN HOLDER APPARATUS AND METHOD

FIELD OF THE INVENTION

This invention relates to a hands free specimen holder apparatus and method. In particular, in accordance with one embodiment, the invention relates to a hands free specimen holder apparatus including a cup holder. An arm is connected with the cup holder at a first end and the arm extends the cup holder from the first end and away from and below a second end. The second end of the arm is conformed to connect with a toilet seat.

BACKGROUND OF THE INVENTION

A difficulty arises in situations where specimens of bodily fluid are required. In particular, but by way of example only and not by limitation, when it is necessary for a female to collect a urine specimen, many difficulties are encountered. The current state of the "art", is a person holds a small specimen cup and attempts to urinate into the cup. This is a difficult thing to do without missing the cup, urinating on yourself or in some way contaminating the specimen that is managed to be collected. These problems are increased in the case of the need to collect a specimen from an elderly, obese, pregnant or incapacitated person. In some situations, men are required to provide a specimen that catches any passed kidney stones, for example only, and this results in difficulties similar to those that women encounter. Further, for court ordered supervised drug testing, it is an issue that the person providing the specimen keeps their hands in plain view to prevent tampering with the specimen. Still further, there is a need to reduce the risk of spreading pathogens from person to person as the specimen is obtained and tested. The state of the prior art at this time is that the specimen, once obtained, is placed on the floor or a counter in order to cap it.

Thus, there is a need in the art for an apparatus and method for collecting a specimen that is easy to use and sanitary. There is a need for a system that is useful in many situations and which enables the collection of an uncontaminated specimen from men as well as women. There is a need for a device that allows a specimen to be obtained while the provider keeps his or her hands in plain view. There is a need for a device that reduces the risk of spreading disease during the process. It, therefore, is an object of this invention to provide an apparatus and method for the collection of a specimen of bodily fluid that does not risk the user coming in contact with the fluid, that is simple to install and easy to use and that is useful for women and men as well.

SUMMARY OF THE INVENTION

Accordingly, the hands free specimen holder apparatus of the present invention, according to one embodiment, includes a cup holder. An arm is connected with the cup holder at a first end and the arm extends the cup holder from the first end and away from and below a second end. The second end of the arm is conformed to connect with a toilet seat.

According to another aspect, a shield is connected with the arm. In another aspect, a basket filter is connected with the arm. In one aspect, the cup holder is connected with the arm at approximately a right angle and such that the cup holder is approximately parallel to the toilet seat. In another aspect, the cup holder includes a pair of cup arms creating a space between them. In a further aspect, the arm includes a slot with a broad opening and a narrow opening and the shield includes a retainer conformed to fit within the broad opening and be retained within the slot. According to one aspect, the retainer includes a spine connected with the shield on a first side and a transverse surface connected with a second side of the spine, the transverse surface being broader than the slot. In another aspect, the second end of the arm includes an upper side and a spaced apart lower side such that the upper side and the lower side connect with the toilet seat on a top of the toilet seat and on a bottom of the toilet seat. In one aspect, the arm includes a slot with a broad opening and a narrow opening and the basket filter includes a retainer conformed to fit within the broad opening and be retained within the slot.

According to another embodiment of the invention, a hands free specimen holder apparatus includes a cup holder. An arm is connected with the cup holder at a first end and the arm extends the cup holder from the first end away from and below a second end. The second end of the arm is conformed to engage a toilet seat and the second end of the arm includes an upper side and a spaced apart lower side such that the upper side and the lower side connect with the toilet seat on a top of the toilet seat and on a bottom of the toilet seat. And, a handle is connected with the second end of the arm.

In another aspect of this invention, a shield is connected with the arm. In a further aspect, the arm includes a slot with a broad opening and a narrow opening and the shield includes a retainer conformed to fit within the broad opening and be retained within the slot. In another aspect, a basket filter is connected with the arm. In a further aspect, the arm includes a slot with a broad opening and a narrow opening and the basket filter includes a retainer conformed to fit within the broad opening and be retained within the slot. In another aspect, the cup holder includes a pair of cup arms creating a space between them. In another aspect, the cup holder is connected with the arm at approximately a right angle and such that the cup holder is approximately parallel to the toilet seat.

According to another embodiment of the invention, a hands free specimen holder method includes the steps of: providing a cup holder with an arm connected with the cup holder at a first end where the arm extends the cup holder from the first end away from and below a second end and with the second end of the arm conformed to connect with a toilet seat; connecting the second end with a toilet seat; and placing a cup in the cup holder.

In another aspect, a shield is connected with the arm. In a further aspect, a basket filter is connected with the arm. In one aspect, the cup holder is connected with the arm at approximately a right angle and such that the cup holder is approximately parallel to the toilet seat.

DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF THE INVENTION

Figure 1:
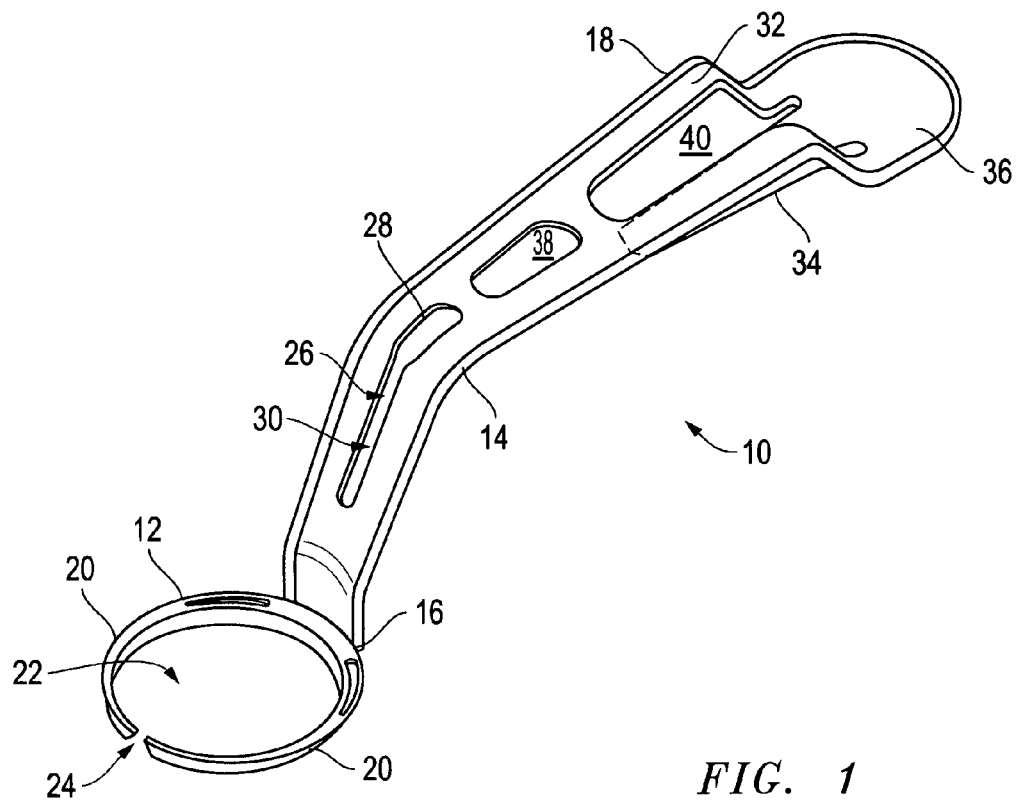
FIG. 1 is a side perspective view of the hands free specimen holder of the present invention according to one embodiment

The preferred embodiment of the present invention is illustrated by way of example in FIGS. 1-4. With specific reference to FIG. 1, hands free specimen holder apparatus 10, according to one embodiment, includes cup holder 12. Arm 14 is connected with cup holder 12 at a first end 16. Arm 14 includes a second end 18 and the invention requires that the arm 14 extends cup holder 12 away from and below the second end 18. That is, as shown in FIG. 1, the length of arm 14 not only separates first end 16 from second end 18 but also angles the separation such that, when observed from the side as in FIG. 1, in use, arm 14 angles down from second end 18 to first end 16. It is understood that, when second end 18 is held in a position that is, for example, when attached horizontal to a surface, the result is that cup holder 12 is extended away from and held below the second end 18 by first end 16.

According to one embodiment, cup holder 12 includes a pair of cup arms 20 connected with first end 16 as shown. In combination, cup arms 20, which preferably are essentially parallel and curved as illustrated, create a space 22 into which a cup (not shown) may be placed and held in place. Obviously, cup arms 20 may not include a gap 24 and could be a continuous, single arm and still create a space 22. However, Applicant has found that gap 24 is useful in enabling hands free specimen holder apparatus 10 to accommodate cups of various dimensions. Further, the pair of cup arms 20 are preferably made of a flexible impervious material such as plastic, for example only, and when a cup is pushed into place in space 22, the resilient nature of the pair of cup arms 20 causes them to apply a compressive force to the cup and help retain the cup in position within space 22. In this regard, again, it should be understood that hands free specimen holder apparatus 10 may be made of resilient plastic or any other sturdy, yet flexible material now known or hereafter developed.

Still referring to FIG. 1, another aspect of the invention is illustrated in which arm 14 includes a slot 26. Slot 26 includes a large broad opening 28 and a narrow opening 30. Broad opening 28 is connected with narrow opening 30 to form slot 26 as illustrated and as will be discussed more fully hereafter with regard to FIGS. 2 and 3.

FIG. 1 also illustrates another aspect of the invention where second end 18 of arm 14 includes an upper side 32 and a spaced apart lower side 34 such that the upper side 32 and the lower side 34 connect with a toilet seat (not shown in this figure) on a top of the toilet seat and on a bottom of the toilet seat as will be more fully described with reference to, and as illustrated in, FIGS. 2-4.

Still referring to FIG. 1, another aspect of the invention includes handle 36. Handle 36 is connected with or formed in second end 18 of arm 14 as shown. Applicant has determined, that handle 36 allows a user to easily attach hands free specimen holder apparatus 10 to a toilet seat and to accurately and easily reposition the apparatus once attached. The ability to "micro-adjust" the invention once attached to a toilet seat is a very useful element of the invention that ensures that a useable specimen is obtained. Further, handle 36 enables a user to adjust the location of the cup holder 12 without coming in contact with the toilet seat or having to place ones hands within the toilet confines.

FIG. 1 also illustrates the aspect of the invention in which it is as light weight as possible but yet sturdy. Thus, FIG. 1 shows a cut out 38 in arm 14 in which some of the material of arm 14 has been removed. In some cases, such as in the cut out 40, the material of arm 14 is only partially cut away from the arm 14. In cut out 40, the lower side 34 is created by making a cut in arm 14 and leaving the lower side 34 connected with the second end 18 of arm 14 at or near handle 36 as shown. In the situation where hands free specimen holder apparatus 10 is made from a pliable plastic, the required shape of the arm 14 and the separation of upper side 32 from lower side 34 can be made after the lower side 34 is partially cut out of arm 14 by heating the plastic, for example only, as is known in the art. Obviously, the entire apparatus may be made from a single piece of material and bent and formed into the required structure.

Figure 2:
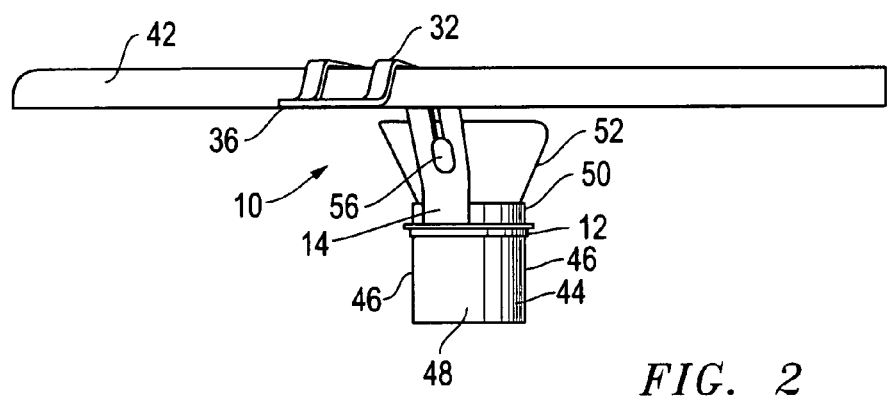
FIG. 2 is a side view of the invention of FIG. 1 as attached to a toilet seat and including a shield.

Referring now to FIG. 2, the hands free specimen holder apparatus 10 is shown attached to a toilet seat 42. Toilet seat 42 is, obviously, to be used with a toilet (not shown) as is known and not described more fully hereafter. FIG. 2 shows a cup 44 held within cup holder 12. Cup 44 may be any cup now known or hereafter developed that fits within cup holder 12 and is designed to retain specimens such as urine, for example only. As shown, cup 44 has parallel sides 46 which means the dimension of cup 44 must be such that cup 44 fits within cup holder 12. Here, the aspect of the invention including a pair of cup arms 20 with a gap 24 enable flexible cup arms 20 to expand slightly to accommodate cup 44 even if cup 44 is slightly larger than the space 22 created by the cup arms 20. Other forms of cup 44 may include sides that taper up and out from a small diameter bottom 48 to a wider top 50 (not shown) such that space 22 accommodates any cup 44 with a bottom 48 smaller than space 22.

FIG. 2 also illustrates shield 52. Shield 52 is useful is guiding the specimen into cup 44. Shield 52 includes a spine 54 (not shown here and more fully shown in FIG. 3) connected with shield 52 and a transverse surface 56 connected with the spine 54. Transverse surface 56 is small enough to fit within broad opening 28 in arm 14 but too large to pass through narrow opening 30 and spine 54 is small enough to fit within narrow opening 30. Thus, shield 52 is easily connected with arm 14 whenever it is needed and deemed useful to the user.

Figure 3:
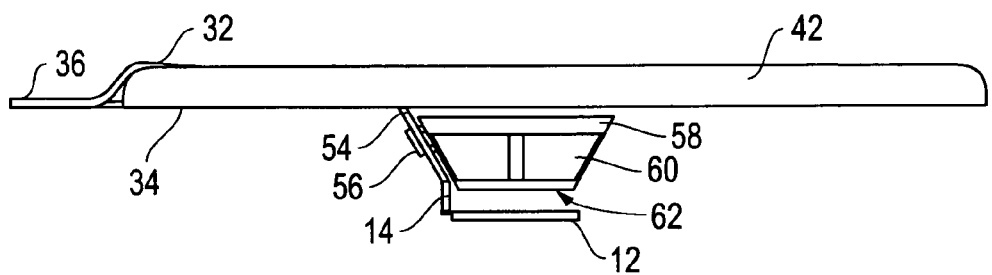
FIG. 3 is a side view of the invention of FIG. 1 as attached to a toilet seat and including a basket filter.

Referring now to FIG. 3, basket filter 58, which includes spine 54 and transverse surface 56 as described above, is connected with arm 14 as described above with regard to shield 52. Basket filter 58 is just that, a basket for capturing material, such as kidney stones for example only, that are contained within the specimen (not shown) such as urine. That is, the sides 60 and bottom 62 (not shown) are made of a filter material such that fluid passes through the filter in the sides 60 and bottom 62 while the specimen is captured in a cup 44 (not shown in this figure) and the stones are captured in the basket filter 58.

Figure 4:
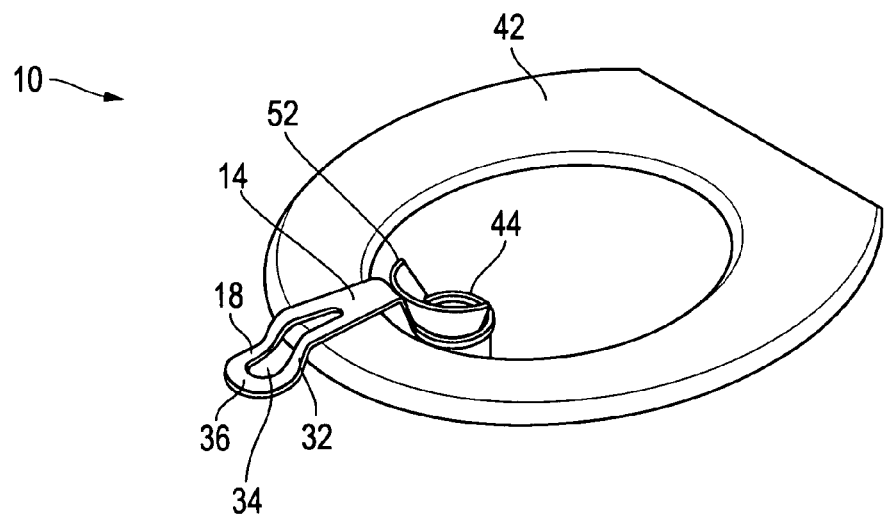
FIG. 4 is a top perspective view of the invention of FIGS. 1 and 2 as attached to a toilet seat.

Referring now to FIG. 4, Applicant's hands free specimen holder apparatus 10 is shown in position connected with a toilet seat 42. One important feature of the invention is shown in which cup 44 is held in place below second end 18 within a toilet (not shown) and below the second end 18 of arm 14. This feature is also clearly shown in FIGS. 2 and 3.

Additionally, FIG. 4 shows handle 36 as extending beyond toilet seat 42 and, again, Applicant has found that it allows a user to position cup 44 precisely where needed with no chance of the user coming in contact with the specimen being taken. Thus, the apparatus 10 may be moved to the front of the toilet seat prior to use or to any other desired location on the toilet seat before, during or after use.

By way of further explanation, for example only, when urine specimens are collected for various clinical reasons, including drug testing and kidney stone retrieval, a woman is presently required to hold the collection device, a cup, in such a way as the likelihood of urine coming in contact with the holder's hand is very high if not certain. Also, when specimens are obtained from geriatric or pediatric patients, a care giver must place their hand into a toilet and hold the cup in the appropriate position to obtain the urine specimen. This is difficult for those trying to fill the cup and for the person holding the cup too. Applicant's invention allows arm 14 to be hooked to the toilet seat 42 such that cup 44 is suspended above the water in the toilet bowel but below the toilet seat 42, thus allowing the user to comfortably sit on the toilet seat and fill the cup 44 without the need of holding the cup themselves or having another person to hold the cup 44 for them, an even more awkward and perhaps embarrassing situation. After use, the user can put their clothing in position and then retrieve the cup 44.

The description of the present embodiments of the invention has been presented for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention as defined by the following claims.

What is claimed is:

1. A hands free specimen holder apparatus comprising:
  a. a cup holder;
  b. an arm connected with the cup holder at a first end and a shield connected with said arm wherein said arm extends said cup holder from said first end away from and below a second end of said arm and wherein said arm includes a slot with a broad opening and a narrow opening and said shield includes a retainer conformed to fit within said broad opening and be retained within said slot and wherein said retainer includes a spine connected with said shield on a first side and a transverse surface connected with a second side of said spine, said transverse surface being broader than said slot; and
  c. the second end of the arm conformed to connect with a toilet seat.

2. The apparatus of claim 1 further comprising a basket filter connected with said arm.

3. The apparatus of claim 2 wherein said arm includes a slot with a broad opening and a narrow opening and said basket filter includes a retainer conformed to fit within said broad opening and be retained within said slot.

4. The apparatus of claim 1 wherein said cup holder is connected with said arm at approximately a right angle and such that said cup holder is approximately parallel to said toilet seat.

5. The apparatus of claim 1 wherein said cup holder includes a pair of cup arms creating a space between them.

6. The apparatus of claim 1 wherein said second end of said arm includes an upper side and a spaced apart lower side such that said upper side and said lower side connect with said toilet seat on a top of said toilet seat and on a bottom of kid toilet seat.

7. A hands free specimen holder apparatus comprising:
  a. a cup holder;
  b. an arm connected with the cup holder at a first end wherein said arm extends said cup holder from said first end away from and below a second end of said arm and a basket filter connected with said arm and wherein said arm includes a slot with a broad opening and a narrow opening and said basket filter includes a retainer conformed to fit within said broad opening and be retained within said slot; and
  c. the second end of the arm conformed to connect with a toilet seat.

8. The apparatus of claim 7 further comprising a shield connected with said arm.

9. The apparatus of claim 8 wherein said arm includes a slot with a broad opening and a narrow opening and said shield includes a retainer conformed to fit within said broad opening and be retained within said slot.

10. The apparatus of claim 9 wherein said retainer includes a spine connected with said shield on a first side and a transverse surface connected with a second side of said spine, said transverse surface being broader than said slot.

11. The apparatus of claim 7 wherein said cup holder is connected with said arm at approximately a right angle and such that said cup holder is approximately parallel to said toilet seat.

12. The apparatus of claim 7 wherein said cup holder includes a pair of cup arms creating a space between them.

13. The apparatus of claim 7 wherein said second end of said arm includes an upper side and a spaced apart lower side such that said upper side and said lower side connect with said toilet seat on a top of said toilet seat and on a bottom of said toilet seat.

\* \* \* \* \*